United States Patent [19]

Haines

[11] Patent Number: 4,536,492

[45] Date of Patent: Aug. 20, 1985

[54] CATALYST FOR THE PREPARATION OF METHYL MERCAPTAN FROM CARBON OXIDES

[75] Inventor: Paul G. Haines, Lafayette Hill, Pa.

[73] Assignee: Pennwalt Corporation, Philadelphia, Pa.

[21] Appl. No.: 584,860

[22] Filed: Feb. 29, 1984

Related U.S. Application Data

[62] Division of Ser. No. 431,858, Sep. 29, 1982, Pat. No. 4,449,006.

[51] Int. Cl.³ .............................................. B01J 27/02
[52] U.S. Cl. .................................. 502/216; 502/219; 502/220; 502/221; 502/222
[58] Field of Search ............... 502/216, 219, 220, 221, 502/222

[56] References Cited

U.S. PATENT DOCUMENTS

| | | | |
|---|---|---|---|
| 3,070,632 | 12/1962 | Olin et al. | 260/609 |
| 4,102,822 | 7/1978 | Mulaskey | 502/220 X |
| 4,389,335 | 6/1983 | Merriam et al. | 502/220 |
| 4,443,330 | 4/1984 | Nongbi | 502/219 X |

FOREIGN PATENT DOCUMENTS 1120499 3/1982 Canada .

OTHER PUBLICATIONS

Shalunenko, N. I. et al., Chemical Abstracts 85:165470w, 1976.

*Primary Examiner*—D. E. Gantz
*Assistant Examiner*—William G. Wright

[57] ABSTRACT

A process is provided for the manufacture of methyl mercaptan with substantial reduction of by-product methane by intimate mixture of carbon oxide, sulfur or hydrogen sulfide and hydrogen at elevated temperature and pressure with a single-phase, solid catalyst system comprising a porous alumina-containing support upon which is deposited a mixture of manganese sulfide and alkali metal sulfide.

4 Claims, No Drawings

CATALYST FOR THE PREPARATION OF METHYL MERCAPTAN FROM CARBON OXIDES

This application is a division of application Ser. No. 431,858, filed Sept. 29, 1982, now U.S. Pat. No. 4,449,006.

BACKGROUND OF THE INVENTION

PRIOR ART DISCUSSION

Methyl mercaptan is a well known article of commerce used as an intermediate for the manufacture of a variety of agricultural chemicals, including methionine, a widely used feed supplement for poultry.

In copending, coassigned application Ser. No. 334,034 filed Dec. 23, 1981 now U.S. Pat. No. 4,410,731, a continuous process for reacting a carbon oxide, sulfur or hydrogen sulfide, and hydrogen at elevated pressure and temperature, is disclosed. The reaction is carried out over a catalyst system comprising a porous alumina-containing support on which is deposited a mixture of a sulfide of iron, nickel, zinc, chromium, cobalt or molybdenum along with an alkali metal sulfide (promoter).

STATEMENT OF THE INVENTION

This invention is a continuous process for the manufacture of methyl mercaptan by contacting an intimate mixture of carbon oxide, sulfur or hydrogen sulfide, and hydrogen at elevated temperature and pressure with a preformed, single-phase, solid catalyst system comprising from about 10 to about 90%, based on the weight of said system, of a porous alumina-containing support and from about 90 to about 10%, based on the weight of said system, of a mixture of:

(a) from about 2 to about 95%, based on the weight of the mixture, of a sulfide of manganese with (b) from 0 to about 90%, based on the weight of the mixture, of at least one sulfide selected from the group consisting of sulfides of iron, nickel, zinc, chromium, cobalt and molybdenum, and (c) from about 5 to about 80%, based on the weight of said mixture, of an alkali metal sulfide, the total of (a), (b), and (c) equaling 100%.

When the amount of (a) is less than 20%, then a sufficient amount of (b) must also be present to provide a total of 20% of (a) and (b) combined.

This invention also comprises the single-phase, solid catalyst system as described above and the method for preparing the system.

DEFINITIONS

Certain terms and phrases used herein have the following meaning with regard to this disclosure.

The term "single-phase, solid catalyst" means a catalytically active mass of intimately mixed components which are solid materials.

The term "hydrogenation catalyst" as used herein means the sulfide of manganese which may be combined with a sulfide of iron, nickel, chromium, cobalt, molybdenum or mixtures of these sulfides. This term also includes the oxides, hydroxides and salts of manganese or such compounds of manganese with the oxides, hydroxides or salts of the above listed metals prior to and after sulfiding whereby they are at least partially converted to the sulfide.

The term "promoter" is used herein means the alkali metal sulfides and hydrosulfides or their oxide, hydroxide or salt precursors prior to or after sulfiding.

The term "catalyst system" as used herein means the combined hydrogenation catalyst, promoter and support.

The term "sulfide" as used herein is defined as a material including simple sulfides and hydrosufides, and complex sulfides.

The term "sulfiding" or "sulfided" as used herein relates to the treatment of the supported mixture of hydrogenation catalyst and promoter, at least one of which is not in the sulfide state, with hydrogen sulfide or vaporous elemental sulfur under elevated temperature for a time such that the mixed materials are at least partially converted to the sulfide. Conversion of either the hydrogenation catalyst or the promoter from the oxide, hydroxide or salt to the sulfide state will change the weight of the compound somewhat but generally will permit, prior to sulfiding, the use of the sulfide precursor within the same weight range as described herein for the sulfide in order to provide a catalyst system as defined for this invention.

The term "space velocity" as used herein, refers to the volume (usually in liters) of carbon oxide passing through a unit volume (usually a liter) of the catalyst system during one hour measured at a standard temperature and pressure.

EXAMPLES

The process of this invention for the production of methyl mercaptan is illustrated by the following examples:

EXAMPLE 1

To prepare the catalyst of this invention, 300 g. of manganese dioxide supported on activated alumina (Harshaw-Mn-0201T) wherein the $MnO_2$ was 19% by weight of the solids, was dried overnight at 150° C. 30 g. of cesium hydroxide in 80 ml. of distilled water was deposited on this dried material such that the solution became evenly distributed throughout the mass. The mass was then dried overnight at 150° C.

250 g. of this dried mass was introduced to a stainless steel reactor tube, 2 inches in diameter and 40 inches long, enclosed in a horizontal furnace. The mass was sulfided by careful heating in a slow stream of hydrogen sulfide diluted with about 80% by volume of nitrogen. An immediate exotherm occurred on contact of the cesium hydroxide. A second, more intense exotherm occurred when the magnanese dioxide reacted with hydrogen sulfide. Maximum temperature of the mass was 321° C. and maximum pressure in the reaction tube was 50 psig during the three-hour sulfiding process. This catalyst, prepared as described above, was designated catalyst A. Catalyst A consists of 71.2% $Al_2O_3$ support and 28.8% additive mixture. The additive mixture consists of 57.6% MnS and 42.4% CsSH.

Catalyst A was used in the production of methyl mercaptan by feeding through separate lines, carbon monoxide (CO), hydrogen ($H_2$), and hydrogen sulfide ($H_2S$) into a preheater (300° C.) where these materials were combined, heated and passed into a fixed bed, tubular, horizontal reactor. Molten sulfur was pumped into the reactor through a separate heated line. The molar feed ratio of $CO/H_2/S/H_2S$ was 1/8/1/5, respectively, and the feed space velocity (as previously defined) was 148.

In the reactor, the catalyst bed temperature reached a maximum of 418° C. during the run and the pressure, maintained by an automatic back-pressure regulator, was 700 psig. The crude product stream was passed as a vapor through heated lines (200° C.) at atmospheric pressure into a gas sampling device of a gas chromatograph for analysis.

For comparison, a preferred catalyst of copending application Ser. No. 334,034, filed Dec. 23, 1981 now U.S. Pat. No. 4,410,731 prepared by sulfiding activated alumina bearing zinc and chromium (Harshaw-ZN-0601T) on which 10% (based on the weight of ZN-0601T) of cesium hydroxide had been deposited, was used to catalyze a similar reaction. The activated alumina bearing zinc and chromium consisted of 38 weight % zinc oxide, 25 weight % chromium oxide and 37 weight % of activated alumina. This material was evenly impregnated with cesium hydroxide in water to provide the stated percentage addition, and then dried and sulfided. Sulfiding was carried out under the same conditions recited above for the manganese containing catalyst except that the maximum catalyst temperature was 330° and the maximum pressure was 50 psig during the three-hour sulfiding procedure. This catalyst was designated catalyst B.

The following comparative results were obtained in a single pass of reactants through the reactor. The single-pass conversion of carbon monoxide to methyl mercaptan (MM) and yields were calculated from the gas chromatographic analyses. The yields, as calculated here, take into account all unreacted starting materials and intermediates that will form methyl mercaptan on recycling.

TABLE 1

| Catalyst | % Conversion, CO to: | | % yield | |
|---|---|---|---|---|
| | $CH_3SH$ | $CH_4$ | $CH_3SH$ | $CH_4$ |
| A (manganese) | 49 | none detected | 91 | none detected |
| B (zinc-chromium) | 44 | 1.3 | 91 | 1.5 |

The advantages of the manganese catalyst A over the zinc-chromium catalyst B are (1) the slightly higher single pass conversion and (2) the elimination of methane as a by-product in this reaction.

EXAMPLE 2

A catalyst, similar to catalyst B of Example 1, but containing sulfided manganese was prepared as follows: 540 g. of the activated alumina bearing zinc and chromium oxides, as described in Example 1, was dried overnight at 150° C. To this dried material was added a solution of 93 g. manganese acetate in 100 ml. of distilled water such that the solution was uniformly distributed in the mass. The material was again dried overnight at 150° C. and then calcined by heating at 450° C. for 5 hours. Analysis of a sample showed 4.87 weight % manganese oxide in the calcined mass. To 270 g. of the calcined material was added a solution of 27 g. cesium hydroxide in 70 ml. of distilled water and the material was dried overnight at 150° C. 250 g. of this dried cesium-containing material was then sulfided as described in Example 1 except that the maximum catalyst temperature was 340° C. and the maximum pressure was 50 psig. This catalyst was designated catalyst C. Catalyst C consists of 27.6% $Al_2O_3$ support and 72.4% additive mixture. The additive mixture consists of 6.2% MnS, 33.9% $Cr_2S_3$, 47.8% ZnS, and 12.1% CsSH.

The above described catalyst C and catalyst B (from Example 1) were used to catalyze reactions using the equipment and process conditions described in Example 1 except that the molar ratio of hydrogen to carbon monoxide in the feed was lowered to 3.5/1. The conversion and yield percentages were determined as in Example 1.

TABLE 2

| Catalyst | % Conversion, CO to: | | % yield | |
|---|---|---|---|---|
| | $CH_3SH$ | $CH_4$ | $CH_3SH$ | $CH_4$ |
| C | 30 | 1.3 | 82 | 2.9 |
| B | 40 | 3.2 | 81 | 4.6 |

Conversion and yield to undesirable by-product methane were lower with the manganese containing catalyst C.

EXAMPLE 3

Manganese containing catalyst A and zinc-chromium containing catalyst B each as described in Example 1, were used to catalyze a reaction for producing methyl mercaptan similar to the procedure of Example 1 except that the carbon oxide reactant was a 1/1 mixture of carbon monoxide and carbon dioxide. The space velocity was 45, based on CO and 45 based on $CO_2$; the reactant molar ratio for $CO/CO_2/H_2/S/H_2S$ was 0.5/0.5/3.5/1/5, respectively; and the catalyst bed temperature was 365° C. (maximum). Determination of conversion and yield percentages were made as in Example 1 and this data is set forth in the following table:

TABLE 3

| Catalyst | % Conversion, CO to: | | % yield (based on CO and $CO_2$) | |
|---|---|---|---|---|
| | $CH_3SH$ | $CH_4$ | $CH_3SH$ | $CH_4$ |
| A | 21 | 1.8 | 93 | 6 |
| B | 30 | 6 | 83 | 14 |

The effectiveness of the manganese catalyst of this invention for producing methyl mercaptan from carbon oxides in high yield while minimizing the amount of objectionable methane produced, is well demonstrated by the data in the above table.

DISCUSSION-GENERIC

The process of this invention is a continuous, vapor-phase reaction wherein a mixture of carbon oxide, hydrogen sulfide or elemental sulfur, and hydrogen is subjected to elevated temperature and pressure in the presence of a specified sulfided or sulfide catalyst system containing manganese to provide methyl mercaptan in improved conversions and yields. Methane formation is kept to a minimum in this process which should result in economy in a commercial operation. Formation of by-product methane is very undesirable because it is an inert material that cannot be separated from the recycle gases. It would build up in the recycle gas stream and would have to be vented periodically, with a loss of valuable raw materials. Generally, higher conversions and yields are obtained with the preferred conditions as set forth below.

The Reactants

Carbon monoxide, hydrogen sulfide or elemental sulfur, and hydrogen are the preferred starting materials for the process of this invention. Carbon dioxide may be used to replace part or all of the carbon monoxide but carbon monoxide is more reactive and provides higher conversions than carbon dioxide at high space velocities.

Carbon monoxide and hydrogen reactants may be inexpensively prepared using the well known "synthesis gas" process which proceeds according to the formula:

$$CH_4 + H_2O \rightarrow CO + 3H_2$$

A supplied hydrogen sulfide may be used in the process or hydrogen sulfide may be formed on site by reacting elemental sulfur in the molten or vapor state with hydrogen to form the hydrogen sulfide either before or after mixing the reactants for feeding to the reactor. Alternatively, elemental sulfur may be fed directly to the reactor with the carbon oxide and hydrogen. Under the temperature and pressure conditions of this process, the sulfur will be in the molten state and will immediately react with hydrogen to form hydrogen sulfide in situ. The chemical equation for the process of this invention when employing elemental sulfur in the feed is one of the following depending on whether CO or $CO_2$ is the carbon oxide of the feed.

$$CO + S + 3H_2 \rightarrow CH_3SH + H_2O$$

$$CO_2 + S + 4H_2 \rightarrow CH_3SH + 2H_2O$$

The reaction sequence by which carbon monoxide is converted to methyl mercaptan is:

$$CO + H_2S \rightarrow COS + H_2 \quad (a)$$

$$COS + 3H_2 \rightarrow CH_3SH + H_2O \quad (b)$$

Reactions (a) and (b) proceed readily using the catalyst system of this invention; reaction between CO and $H_2$ to produce methanol does not occur.

Process Conditions

The feed rate of the reactants through the catalyst bed of the reactor is reported herein as space velocity of carbon oxide. The optimum space velocity employed will vary between about 20 and about 300 depending upon other conditions of the process such as temperature, pressure and molar ratio of reactants. In general, high conversions are realized with low space velocities. The preferred space velocity range is about 20 to 200. In commercial practice, where high production rates are desired, this process can be operated at high space velocities in the range of 60-200 with relatively high conversions to methyl mercaptan per pass.

The molar ratio of reactants in the feed mixture, i.e., carbon oxide, hydrogen sulfide or elemental sulfur, and hydrogen, is not a critical feature of the process. The ratio of reactants consumed is that theoretically required to form methyl mercaptan by the direct conversion of these reactants. Preferably the carbon oxide will be fed to the reactor with a molar excess of both hydrogen sulfide and hydrogen. Most preferably, molar ratios of $CO_{1-2}/H_2S/H_2$ between 1/3/2 and 1/8/8 are used. When utilizing elemental sulfur to replace $H_2S$ in the feed, the molar ratio of the reactants $CO_{1-2}/S/H_2$ will preferably range from about 1/3/3 to about 1/8/10.

The reactants are preferably mixed in the desired molar ratio before being passed to the reactor but they may also be introduced separately to the reactor at a rate and amount to produce the desired molar ratio and space velocity.

To increase the conversions and yields in the process, the reactants are advantageously preheated to at least 150° C. either individually or as a mixture prior to entering the reactor. The preferred preheating range is from about 180° to about 300° C.

The pressure in the reactor is generally above 150 psig. and preferably within the range of about 400 to about 1000 psig., the pressures of this range increasing the conversion to methyl mercaptan.

Temperature in the reactor is generally controlled by the temperature of the catalyst bed which preferably ranges between about 300° C. and 425° C. In addition to the exothermic heat of reaction, further heat is supplied externally.

Broadly, when sulfur is used as a reactant in the process, the temperature and pressure in the reactor should be at least sufficient to maintain the sulfur in the molten state.

The Catalyst System

The catalyst system for the process of this invention is a preformed material, i.e., it is mixed and, if necessary, sulfided prior to the introduction of the process reactants to the reactor. The catalyst system required for the process consists of a manganese containing hydrogenation catalyst in the sulfide form, a promoter in the sulfide form, and a porous support. The hydrogenation catalyst and promoter, as broadly used in this disclosure, have been defined hereinbefore. The preferred hydrogenation catalyst are those containing the sulfide of manganese alone or the manganese sulfide combined with the sulfide of zinc and chromium where the mixture is no greater than about 35 weight percent of manganese sulfide, up to about 55 weight percent zinc sulfide and up to about 40 weight percent chromium sulfide.

Potassium, rubidium and cesium are the preferred alkali metals, in the sulfide form, for the promoter and cesium is the most preferable.

The proportion of hydrogenation catalyst used in admixture with the alkali metal promoter preferably ranges from about 80 to 95 percent, based on the weight of the admixture, while the proportion of the alkali metal promoter ranges from about 20 to about 5 percent.

The hydrogenation catalyst and promoter are carried on a suitable porous support comprising alumina which may be, for example, activated alumina or alumina containing materials, e.g., silica-alumina, various alumina containing clays or refractory materials; and the like. Activated alumina is the preferred support for the catalyst system.

The support which carries the catalyst and promoter is preferably from about 15 to about 80 percent by weight of the catalyst system and the hydrogenation catalyst-promoter mixture is present in an amount ranging from 85 to 20% of the catalyst system.

Usually, a support bearing the hydrogenation catalyst is obtained from a commercial source and impregnated with a solution of the promoter as shown in the working examples herein. While the hydrogenation catalyst is frequently obtained from the supplier on a support, either the hydrogenation catalyst or the promoter may be first deposited on a support and other component of the catalyst system subsequently incorporated with the supported component or, alternatively, both materials are deposited simultaneously.

Sulfiding the catalyst system is required where one or both of the hydrogenation catalyst and promoter are not in the sulfide form i.e., they are in the oxide, hydroxide or other salt form. In carrying out a conventional sulfiding step the metal bases on the support are at least partially converted to the sulfide on treatment with H$_2$S or elemental sulfur and hydrogen, if required, at elevated temperature. In the preferred sulfiding process, the dried catalyst-promoter-support system, as described above, is charged to the process reactor to form a bed. Hydrogen sulfide gas is passed through the bed at about 300°–390° C. under atmospheric or elevated pressure for several hours (e.g. 6–8 hours) until water of reaction is no longer present in the effluent gas stream. The sulfided catalyst system is then ready to use in the process.

The above described process provides good conversions and yields of methyl mercaptan with low reaction times and reduced formation of undesirable by-product methane.

What is claimed is:

1. A composition of matter comprising a solid catalyst system of from 10 to about 90%, based on the weight of said system, of a support comprising alumina upon which is deposited from about 90 to about 10%, based on the weight of said system, of a mixture of:
   (a) from 2 to 95%, based on the weight of said mixture, of the sulfide of manganese,
   (b) from 0 to 90% of at least one sulfide selected from the group consisting of sulfides of iron, nickel, zinc and chromium, and
   (c) from 5 to 80%, based on the weight of said mixture, of an alkali metal sulfide, the total of (a), (b) and (c) equaling 100%.

2. The composition of claim 1 wherein said support is activated alumina.

3. The composition of claim 2 wherein component (b) of said mixture is a mixture of 50 to 65 weight % zinc sulfide and 35 to 50 weight % of chromium sulfide.

4. The composition of claim 1, 2 or 3 wherein the alkali metal sulfide of component (c) is cesium sulfide.

* * * * *